US006285179B1

United States Patent
Kubo et al.

(10) Patent No.: US 6,285,179 B1
(45) Date of Patent: Sep. 4, 2001

(54) DETECTING APPARATUS AND DETECTING METHOD OF ABSORBED HYDROGEN AMOUNT IN HYDROGEN ABSORBING TANK

(75) Inventors: Hidehito Kubo, Kariya; Masuhiro Yamaguchi, Yokohama, both of (JP)

(73) Assignee: Kabushiki Kaisha Toyoda Jidoshokki Seisakusho, Kariya (JP)

( * ) Notice: Subject to any disclaimer, the term of this patent is extended or adjusted under 35 U.S.C. 154(b) by 0 days.

(21) Appl. No.: 09/404,991

(22) Filed: Sep. 22, 1999

(30) Foreign Application Priority Data

Sep. 25, 1998 (JP) .................................................. 10-270984

(51) Int. Cl.[7] .......................... G01N 27/00; G01R 27/08; C22C 6/24
(52) U.S. Cl. ........................ 324/71.1; 324/691; 324/693; 420/900
(58) Field of Search .................... 324/71.1, 693; 204/433, 157.1; 205/790; 73/31.05, 23.2; 420/900; 429/218.2; 422/88, 98

(56) References Cited

U.S. PATENT DOCUMENTS

| | | | |
|---|---|---|---|
| 4,233,127 | * 11/1980 | Monahan | 204/157.1 R |
| 4,788,491 | * 11/1988 | Ayers | 324/71.1 |
| 5,668,301 | * 9/1997 | Hunter | 73/23.2 |
| 6,155,099 | * 12/2000 | Kobayashi | 73/31.05 |

FOREIGN PATENT DOCUMENTS 5-10211  1/1993  (JP) .
6-206701  7/1994  (JP) .

OTHER PUBLICATIONS

Journal of Alloys and Compounds 231 (1995), pp. 182–187.

\* cited by examiner

*Primary Examiner*—Safet Metjahic
*Assistant Examiner*—Anjan K Deb
(74) *Attorney, Agent, or Firm*—Morgan & Finnegan, LLP

(57) ABSTRACT

This invention relates to a detecting method and a detecting apparatus for detecting an absorbed hydrogen amount in a hydrogen absorbing tank. An object of the present invention is to to provide a detecting method and a detecting apparatus of absorbed hydrogen amount in a hydrogen absorbing tank, which can detect a hydrogen occlude condition in the hydrogen absorbing tank accurately, irrespective of repeating the absorption and desorption of the hydrogen to and from the hydrogen absorbing tank. In order to achieve the above object, the detecting method in the hydrogen absorbing tank comprises a contain step for containing a hydrogen absorbing alloy powder of a predetermined amount in a hydrogen absorbing tank so that a hydrogen gas comes in the hydrogen absorbing tank from external and goes out therefrom to the external, in the predetermined amount of the hydrogen absorbing alloy powder a contact condition between adjacent hydrogen absorbing alloy powders changing due to a volume expansion of the hydrogen absorbing alloy powder in occluding a hydrogen; a measure step for measuring an electrical resistance value between a pair of detect electrodes provided in the hydrogen absorbing tank; and a determine step for determining an absorbed hydrogen amount in the hydrogen absorbing tank based on a change of the electrical resistance value.

15 Claims, 3 Drawing Sheets

DETECTING APPARATUS AND DETECTING METHOD OF ABSORBED HYDROGEN AMOUNT IN HYDROGEN ABSORBING TANK

DETAILED EXPLANATION OF THE INVENTION

1. Field of the Invention

This invention relates to a detecting method and a detecting apparatus for detecting an absorbed hydrogen amount in a hydrogen absorbing tank.

2. Related Background Art

Conventionally, an absorbed hydrogen amount in a hydrogen absorbing tank filled with hydrogen absorbing alloy powder is detected as shown in Japanese Unexamined (Koukai) Patent No.5-10211, for example. In this prior art, an amount of a hydrogen gas coming in a hydrogen absorbing tank and going out therefrom is detected by a gas flow-amount sensor, and the detected results are accumulated.

However, the hydrogen gas flow-amount sensor inevitably has a measuring error. So, when occludes (absorption) and desorption of the hydrogen to or from the hydrogen absorbing tank are repeated, the accumulated error of the absorbed hydrogen amount becomes large, so that a detecting accuracy by the hydrogen gas flow-amount sensor will be deteriorated. This deterioration of the detecting accuracy may cause some problems in a vehicle and the like which use the hydrogen gas as a fuel.

SUMMARY OF THE INVENTION

The present invention is made in view of the above circumstances, and accordingly has an object to provide the detecting method and the detecting apparatus of absorbed hydrogen amount in the hydrogen absorbing tank, which can detect the hydrogen occlude condition in the hydrogen absorbing tank accurately, irrespective of repeating the absorption and desorption of the hydrogen to and from the hydrogen absorbing tank.

In order to achieve the above object, the detecting method of the absorbed hydrogen amount in the hydrogen absorbing tank of the present, and the detecting apparatus used therefor invention use the following principle. That is, when expansion of the hydrogen absorbing alloy powder occurs with a change of an absorbed hydrogen amount, a contact area and a contact condition of adjacent hydrogen absorbing alloy powders change, so that electrical resistance between electrodes also changes. In view of the above, a relation between the absorbed hydrogen amount of the hydrogen absorbing alloy powder in the hydrogen absorbing tank and the electrical resistance between the both electrodes is mapped in advance, and this relation is used together with a detected electrical resistance value to calculate the absorbed hydrogen amount.

According to these detecting methods and the detecting apparatus, even if the absorption and desorption or the hydrogen to and from the hydrogen absorbing tank are repeated in many times, the measuring error will not be accumulated, different from the above mentioned conventional art. Thus, the high accuracy detection of the absorbed hydrogen amount in the hydrogen absorbing tank can be realized.

The hydrogen absorbing tank preferably has rigidity to generate a compress stress in the hydrogen absorbing alloy powder in increasing the absorbed hydrogen amount thereof, in other words, to restrict a volume expansion of the hydrogen absorbing alloy powder in occluding the hydrogen. By usage of such hydrogen absorbing tank, since a change rate of the contact area and contact condition between the adjacent hydrogen absorbing alloy powders due to a change of the absorbed hydrogen amount becomes larger, the electrical resistance value between both electrodes can be changed larger, so that a detecting sensitivity of the absorbed hydrogen amount by the detecting method and the detecting apparatus can be further improved.

In the detecting apparatus of a preferred embodiment, the hydrogen absorbing tank contains a predetermined amount of hydrogen absorbing alloy powder which the electrical resistance value changes suddenly when the absorbed hydrogen amount substantially corresponds to a saturated occlude amount. According to this detecting apparatus, the hydrogen occlude saturated condition of the hydrogen absorbing tank is judged by detecting the sudden change of the electrical resistance value.

In the detecting apparatus of the other preferred embodiment, the hydrogen absorbing tank contains a predetermined amount of the hydrogen absorbing alloy powder which the electrical resistance value changes suddenly when the absorbed hydrogen amount substantially corresponds to an absorbed non-hydrogen amount. According to this detecting apparatus, the non-hydrogen occlude condition of the hydrogen absorbing tank is judged by detecting the sudden change of the electrical resistance value.

In the detecting apparatus of the other preferred embodiment, the determining means determines the absorbed hydrogen amount in the hydrogen absorbing tank by substituting the detected electrical resistance value to a map which shows the relation between the electrical resistance value and the absorbed hydrogen amount. According to this detecting apparatus, the present or newest absorbed hydrogen amount can be detected without accumulation of the measured errors.

In the detecting apparatus of the other preferred embodiment, the hydrogen absorbing tank is comprised of a capsule for detecting the absorbed hydrogen amount contained in a main tank which contains a large amount of hydrogen absorbing alloy powder to allow the come-in and go-out of the hydrogen gas relative to the hydrogen absorbing tank. In this detecting apparatus, the problem that when the main tank has small rigidity, the volume thereof expands due to increase of the absorbed hydrogen of the hydrogen absorbing alloy powder contained in the main tank, so that increase of the contact area between the hydrogen absorbing alloy powders in the main tank is restricted irrespective of volume expansion of such hydrogen absorbing alloy powder, is taken into consideration. In view of the above, a hydrogen absorbing tank (capsule) which has an extremely smaller volume than an inner space of the main tank is provided for detecting the absorbed hydrogen amount in the hydrogen absorbing tank accurately. As a result, a large size main tank can be manufactured easily and weight thereof can be reduced to half.

In the detecting apparatus of the other preferred embodiment, the same advantage described above can be obtained.

In the detecting apparatus of the other embodiment, the hydrogen absorbing tank includes a first hydrogen absorbing tank containing the amount of the hydrogen absorbing alloy powder which the electrical resistance value changes suddenly when the absorbed hydrogen amount corresponds to a saturate amount substantially, and a second hydrogen absorbing tank containing the amount of the hydrogen absorbing alloy powder which the electrical resistance value changes suddenly when the absorbed hydrogen amount corresponds to zero substantially. As a result, both of two important conditions i.e. hydrogen occlude saturated condition and non-hydrogen occlude condition for the hydrogen absorbing tank can be accurately detected.

Finally, in the detecting apparatus of the other embodiment, the main tank can be used for one of the first and second hydrogen absorbing tanks, so that the number of capsules contained in the main tank can be reduced.

PREFERRED EMBODIMENT OF THE PRESENT INVENTION

Next, preferred embodiments of the present invention will be explained with reference to attached drawings. However, it is noted that the present invention is not limited to these embodiments, but can include various variations or modifications within the spirit thereof.

Figure 1:
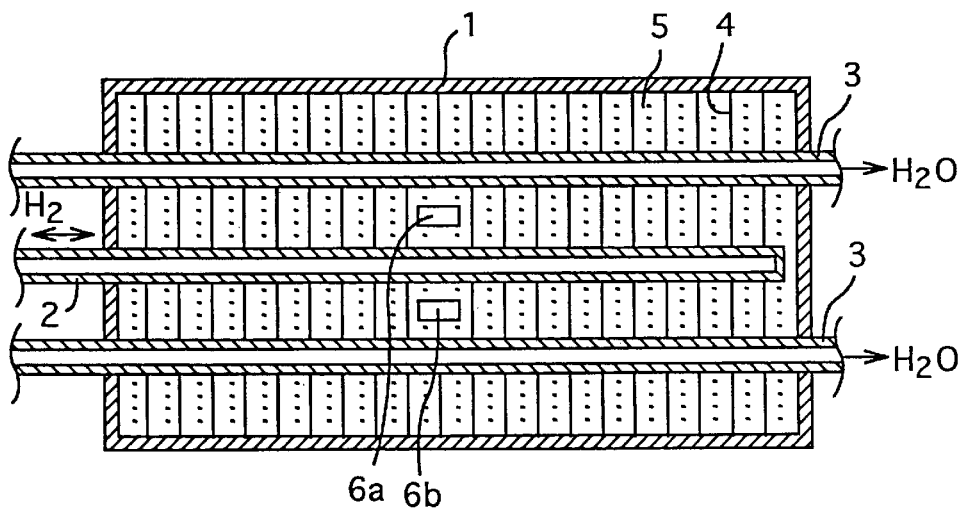
FIG. 1 is a schematic cross-section of the hydrogen absorbing tank according to one embodiment of the present invention.

Firstly, a hydrogen absorbing tank 1 to which an absorbed hydrogen amount detecting device of the present invention is applied, will be explained based on FIG. 1.

In the hydrogen absorbing tank (main tank) 1 made of a stainless steel, porous hydrogen come-in/go-out pipes 2 and heat medium pipes 3 both penetrating the hydrogen absorbing tank 1 axially are provided. Many fins 4 are attached to the heat medium pipes 3 and extending radially in the hydrogen absorbing tank 1 to divide a space of the hydrogen absorbing tank 1 into many small chambers. Each of the small chambers is filled with a hydrogen absorbing alloy powder 5. At a central portion of the hydrogen absorbing tank 1, two hydrogen occlude capsules (hydrogen absorbing tank) 6a and 6b are contained.

Figure 2:
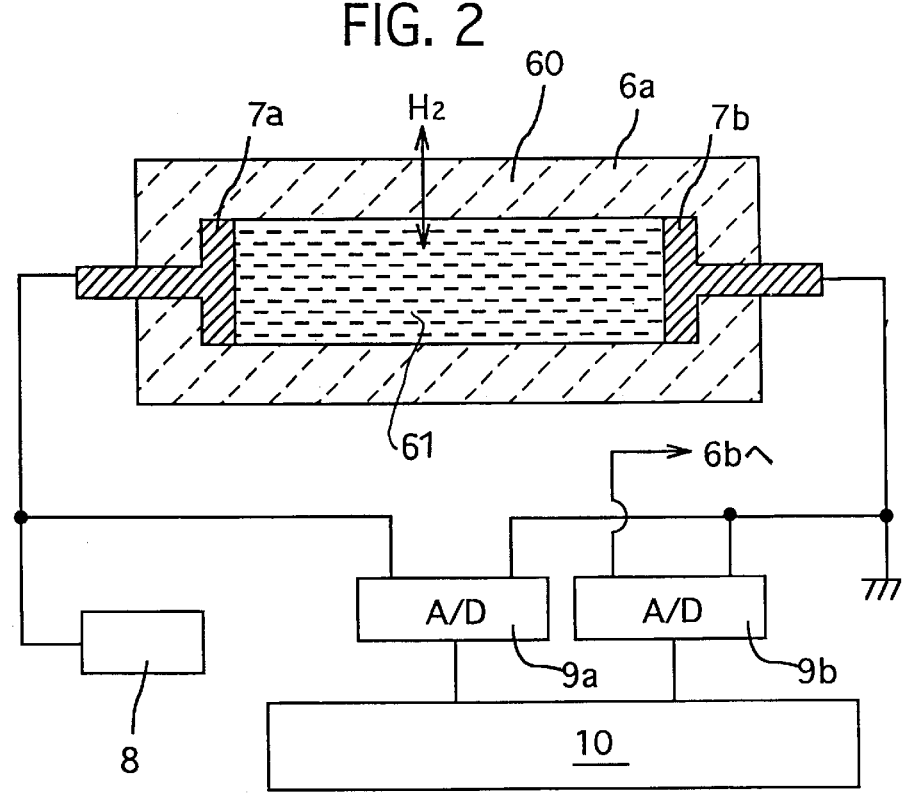
FIG. 2 is a schematic cross-section of a hydrogen occlude capsule 6 used in the above embodiment.

One hydrogen occlude capsule 6a, as shown in FIG. 2, has a porous ceramics tube 60 of which an inner cavity is filled with hydrogen absorbing alloy powder for monitor 61 which has similar characteristic to the hydrogen absorbing alloy powder 5 in the hydrogen absorbing tank 1. At both inner end surfaces of the ceramics tube 60, a pair of elctrode members 7a and 7b are attached and connected to an external device via insulative coated cable (not shown in FIG. 1). Other hydrogen occlude capsule 6b has same construction and the shape as the capsule 6a, so the explanation thereof will be omitted.

To one elctrode member 7a constant current is supplied from a constant current source 8, and other elctrode member 7b is grounded. A signal voltage consisting of a voltage drop between both elctrode members 7a, 7b which is proportional to an electrical resistance between the both elctrode members 7a, 7b, is converted to a digital signal by a A/D convertor 9a and 9b and then is inputted into a controller 10 which has a micro-computer therein. Inner cavity volumes of the hydrogen occlude capsules 6a, 6b are so selected that they do not expand irrespective of expansion of the hydrogen absorbing alloy powder for monitor 61 contained in the hydrogen occlude capsules 6a, 6b, but some compression stress is generated in the hydrogen absorbing alloy 5 in expanding the volume of the hydrogen absorbing alloy powder for monotor 61.

Next, a function of the hydrogen occlude capsule 6a, 6b will be explained.

Figure 3:
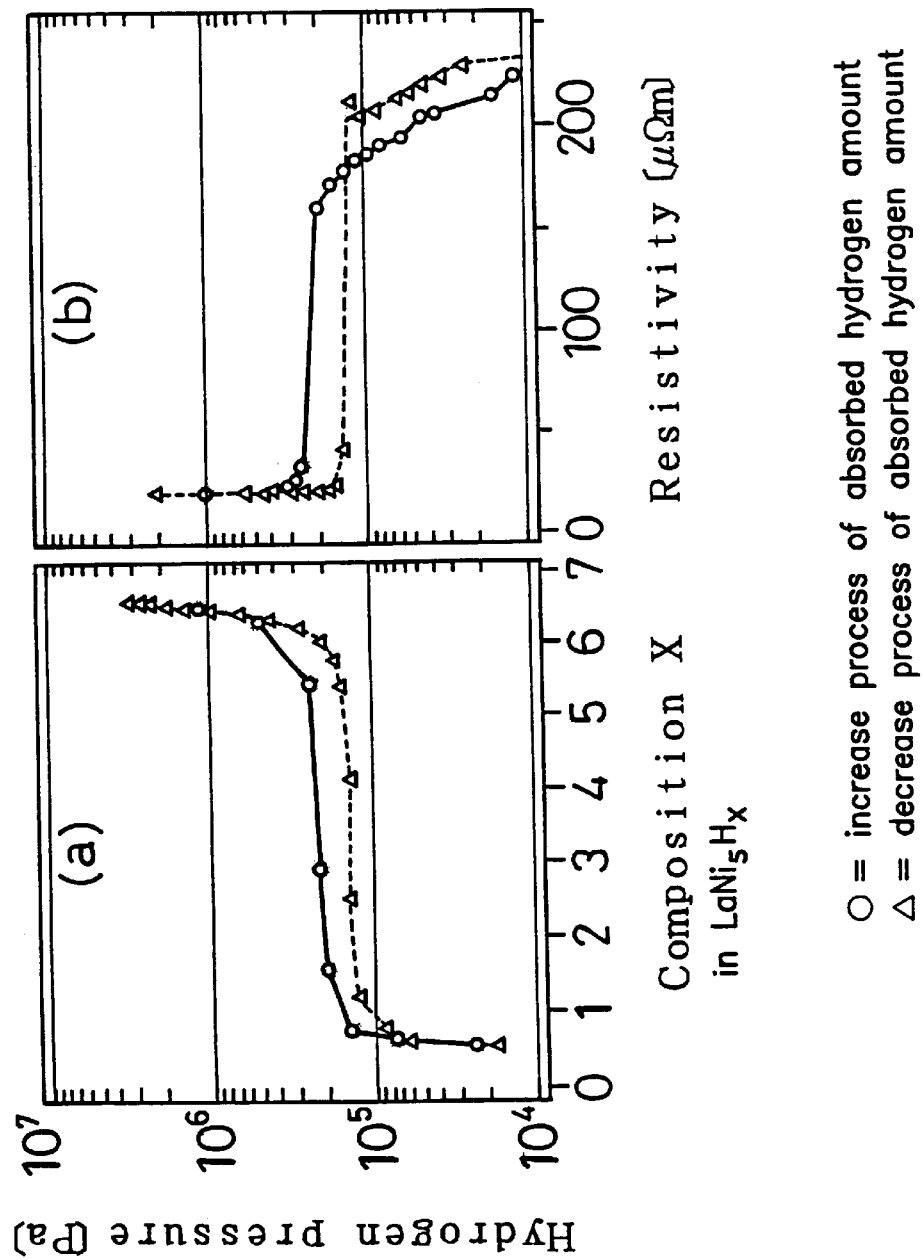
FIG. 3 is a characteristic diagram showing a relation between an absorbed hydrogen amount, and an electrical resistance value between both electrode layers 7a, 7b of the hydrogen occlude capsule 6a, 6b in the above embodiment.

FIG. 3 shows a relation between the absorbed hydrogen amount in the hydrogen acclude capsules 6a, 6b, and the electrical resistance value between the both elctrode members 7a, 7b at the temp. of 20° C., when the hydrogen occlude capsules 6a, 6b which have substantially constant volume are filled with the hydrogen absorbing alloy powder for monitor 61. Here, $LaNi_5H_x$ is used for the hydrogen absorbing alloy powder for monitor 61. Therefore, x shows a rate of the hydrogen atom H in the $LaNi_5H_x$. In FIG. 3, small circles show the characteristic of the hydrogen absorbing alloy powder for monitor 61 in the increase process of the absorbed hydrogen amount, and small triangles show the characteristic of the hydrogen absorbing alloy powder for monitor 61 in the decrease process of the absorbed hydrogen amount.

As apparent from FIG. 3, in both of the increase and decrease process of the absorbed hydrogen amount, in the range of about 1.3 to 4.2 of x showing the absorbed hydrogen amount in the hydrogen absorbing alloy powder 5, the electrical resistance value (resistivity) is changed suddenly (from about 30 to about 170 $\mu\Omega m$).

From the resistivity characteristic shown in FIG. 3, the follow matters can be assumed.

A change of the electrical resistance value of the hydrogen absorbing alloy powder for monitor 61 due to change of the x can be ignored. So, the change of the electrical resistance value is not resulted from the change of an absolute value of the x which shows a composition ratio of the hydrogen absorbing alloy powder for monitor 61, but is resulted from change of the electrical contact resistance between adjacent hydrogen absorbing alloy powders for monitor 61 in the hydrogen occlude capsules 6a, 6b, and the change of the electrical contact resistance between the electrode members 7a, 7b and the hydrogen absorbing alloy powder for monitor 61.

Provided that the volume of the hydrogen occlude capsules 6a, 6b is constant, when the absorbed hydrogen amount (here, it corresponds to x) is maximum and the hydrogen absorbing alloy powder for monitor 61 has the maximum volume, it is assumed that the hydrogen absorbing alloy powder for monitor 61 expands to fill spaces inside of a hydrogen occlude material, so that the spaces between the hydrogen absorbing alloy powders for monitor 61 become minimum and the electrical resistance between the electrode members 7a, 7b becomes minimum.

From the above condition, when the absorbed hydrogen amount of the hydrogen absorbing alloy powder for monitor 61 decreases and the hydrogen absorbing alloy powder for monitor 61 shrinks, it is assumed that a compress stress which presses the contact surface of the adjacent hydrogen absorbing alloy powders for monitor 61 against each other vanishes, so that the electrical contact resistance therebetween starts to increase, at some point. Such increase of the electrical contact resistance of the hydrogen absorbing alloy powder for monitor 61 will occur simultaneously at each of the hydrogen absorbing alloy powders for monitor 61, so that the electrical resistance between the electrode members 7a, 7b will increase suddenly from the preceding minimum value. Of course, current routes or passages are not interrupted, but only the electrical contact resistance increases by vanish of the press force between the adjacent hydrogen absorbing alloy powders for monitor 61.

Then, by further decrease of the absorbed hydrogen amount in the hydrogen absorbing alloy powder for monitor 61, the adjacent hydrogen absorbing alloy powders for monitor 61 start to separate from each other so that the cross-section area of the current routes gradually decrease as a whole. Thus, as decrease of the absorbed hydrogen amount, the electrical resistance value increases.

After all, it is recognized that when the volume of the hydrogen absorbing alloy powders for monitor 61 is changed in the hydrogen occlude capsules 6a, 6b of substantially constant volume, there exist in the electrical resistance value, a saturate area where the electrical resistance value is saturated by strong press between the adjacent hydrogen absorbing alloy powders for monitor 61, a succeeding sudden-change area where the electrical resistance value changes gradually by start of separate-away of the adjacent hydrogen absorbing alloy powders for monitor 61. Accordingly, by adjusting the filled amount of the hydrogen absorbing alloy powder for monitor 61 in the hydrogen occlude capsules 6a, 6b, the absorbed hydrogen amount at the point where the electrical resistance value suddenly changes can be set.

In this embodiment, in one hydrogen occlude capsule 6a, the filled amount of the hydrogen absorbing alloy powder for monitor 61 is set so that the electrical resistance value suddenly changes at the point where the absorbed hydrogen amount is substantially zero; and in other hydrogen occlude capsule 6b, the filled amount of the hydrogen absorbing alloy powder for monitor 61 is set so that the electrical resistance value suddenly changes at the point where the absorbed hydrogen amount is substantially 100%. According to such arrangement, the substantial zero condition and the substantial 100% condition of the absorbed hydrogen amount, in the hydrogen absorbing tank 1 can be easily detected.

Figure 4:
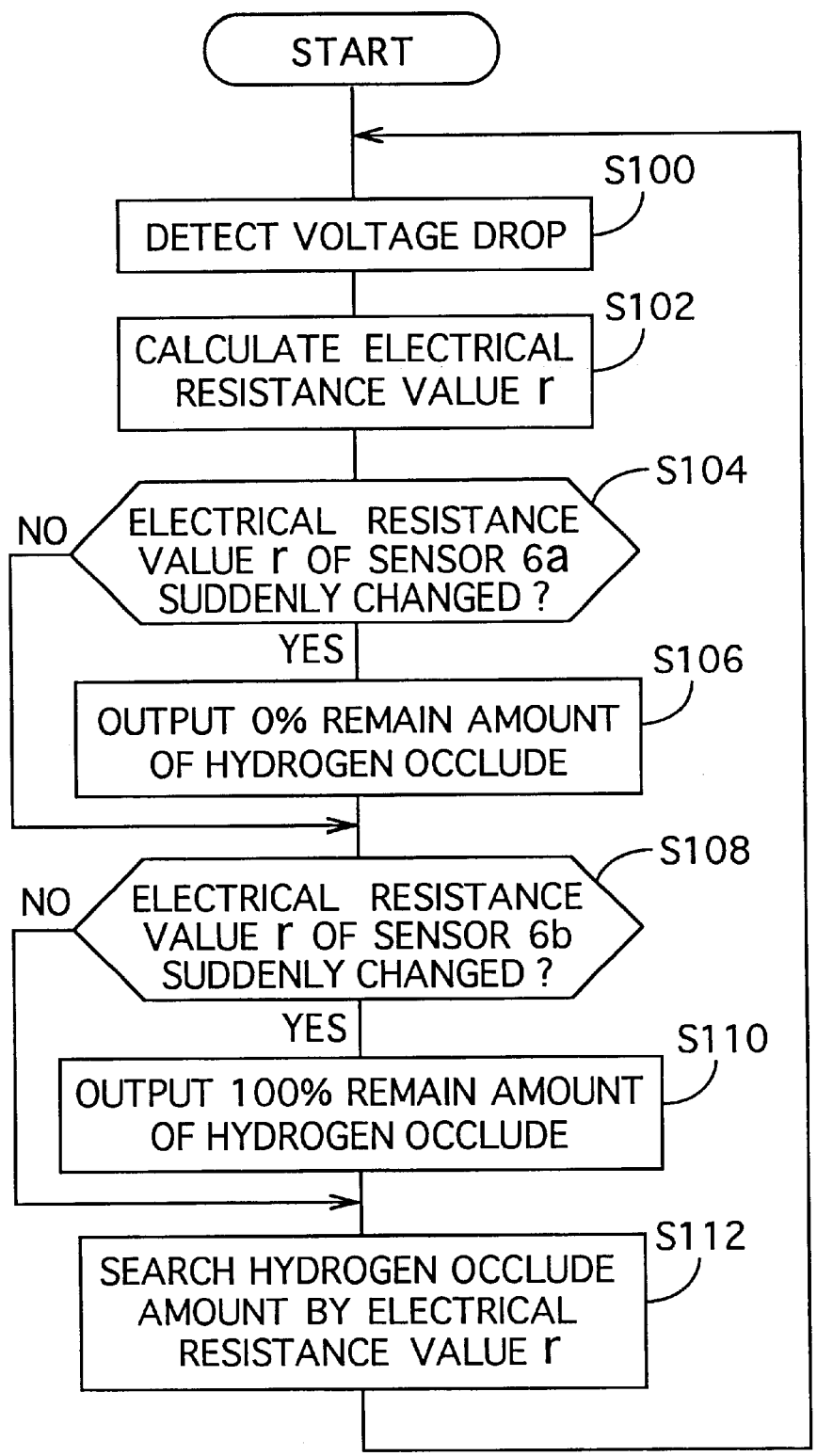
FIG. 4 is a flow-chart showing a detecting process of the absorbed hydrogen amount of the control device (a controller 10) shown in FIG. 2.

Next, a determining operation of the absorbed hydrogen amount performed by a controller 10 will be explained with reference to FIG. 4.

The controller 10, reads in at a step S100 a voltage value proportional to the electrical resistance value r between the elctrode members 7a, 7b from a A/D convertors 9a, 9b, and converts the voltage value in electrical resistance value r at a step S102. The controller 10 then judges at a step S104 whether the electrical resistance value r of the hydrogen occlude capsule 6a is chaneged suddenly or not, in order to detect the substantially zero condition of the absorbed hydrogen amount and outputs at a step S106 the substantially zero condition of the absorbed hydrogen amount in the hydrogen occlude capsule 6a if the sudden change is detected.

The controller 10 then judges at a step S108 whether the electrical resistance value r of the hydrogen occlude capsule 6b is changed suddenly or not, in order to detect the substantially 100% condition of the absorbed hydrogen amount is changed suddenly or not, and outputs at a step S110 the substantially 100% condition of the absorbed hydrogen amount in the hydrogen occlude capsule 6b if the sudden change is detected.

In the controller 10, a map which shows the relation between the detected electrical resistance value and the absorbed hydrogen amount is stored in a memory thereof in advance, and the present or newest electrical resistance value r detected by the step S102 is substituted to this map to search the absorbed hydrogen amount at a step S112. According to the above process, the absorbed hydrogen amount in the hydrogen occlude capsule 6a can be always assumed accurately without generating any accumulated error of the measurement.

It is noted, in this embodiment, the hydrogen absorbing tank 1 and the hydrogen occlude capsules 6a and 6b are constructed so that the hydrogen can flow therebetween, and the hydrogen absorbing alloy powder for monitor 61 in the hydrogen absorbing tank 1 and the hydrogen absorbing alloy powder for monitor 61 in the hydrogen occlude capsules 6a, 6b have the same or equivalent characteristic. For this reason, the absorbed hydrogen amount per a unit weight of the hydrogen absorbing alloy powder for monitor 61 in the hydrogen occlude capsules 6a, 6b can be assumed to be equal to that of the hydrogen absorbing alloy powder for monitor 61 in the hydrogen absorbing tank 1.

Another embodiment of the present invention variation of the detecting apparatus for the absorbed hydrogen amount in the hydrogen absorbing tank 1) will be explained.

1) In the above embodiment, the absorbed hydrogen amount in the hydrogen absorbing tank 1 is not detected by the paired hydrogen occlude capsules 6a, 6b, but a pair of electrodes spaced by a predetermined distance can be provided in the hydrogen absorbing tank 1, instead of the hydrogen occlude capsules 6a, 6b. In this variation, the absorbed hydrogen amount in the hydrogen absorbing tank can be detected based on the electrical resistance value between the paired electrodes. Here, the hydrogen absorbing tank 1 itself can form one electrode which is grounded to make construction of the whole detecting apparatus simpler.

2) A change of relation between the absorbed hydrogen amount and the electrical resistance value by the characteristic change of the hydrogen absorbing alloy powder due to repeating charge/discharge can be memorized in the map in advance, and the absorbed hydrogen amount in the hydrogen absorbing tank 1 which is assumed by the above system or process can be corrected based on the map. According to such a variation, the electrical resistance value can be corrected by powdering of the hydrogen absorbing alloy powder for monitor 61 due to repeating charge/discharge of the hydrogen, so that the change of the electrical resistance value can be corrected.

What is claimed is:

1. An absorbed hydrogen amount detecting method in a hydrogen absorbing tank, comprising steps of:

a step for containing a hydrogen absorbing alloy powder of a predetermined amount in a hydrogen absorbing tank so that a hydrogen gas comes in the hydrogen absorbing tank from an external and goes out therefrom to the external, in the predetermined amount of the hydrogen absorbing alloy powder a contact condition between adjacent hydrogen absorbing alloy powders changing due to a volume expansion of the hydrogen absorbing alloy powder in occluding a hydrogen;

a step for measuring an electrical resistance value between a pair of detect electrodes provided in the hydrogen absorbing tank; and a step for determining an absorbed hydrogen amount in the hydrogen absorbing tank based on a change of the electrical resistance value detected by said measure step.

2. An absorbed hydrogen amount detecting apparatus in a hydrogen absorbing tank, comprising:

a hydrogen absorbing tank containing a hydrogen absorbing alloy powder of a predetermined amount therein so that a hydrogen gas comes in the hydrogen absorbing tank from an external and goes out therefrom to the external, in the predetermined amount of the hydrogen absorbing alloy powder a contact condition between adjacent hydrogen absorbing alloy powders changing due to a volume expansion of the hydrogen absorbing alloy powder in occluding a hydrogen;

a pair of detecting electrodes disposed in said hydrogen absorbing tank at both sides of the hydrogen absorbing alloy powder in said hydrogen absorbing tank;

a voltage source for applying a predetermined voltage between said pair of detecting electrodes;

a detecting means for detecting a condition amount corresponding to an electrical resistance value between said pair of detecting electrodes; and a calculating means for determining an absorbed hydrogen amount in said hydrogen absorbing tank based on the condition amount detected by said detecting means.

3. An absorbed hydrogen amount detecting apparatus according to claim 2, wherein said hydrogen absorbing tank contains an amount of the hydrogen absorbing alloy powder which the electrical resistance value suddenly changes when the absorbed hydrogen amount corresponds to a substantial saturate occlude amount, and said calculating means judges a substantial saturate occlude saturated condition when detecting sudden change of the electrical resistance value.

4. An absorbed hydrogen amount detecting apparatus according to claim 2, wherein said hydrogen absorbing tank contains an amount of the hydrogen absorbing alloy powder which the electrical resistance value suddenly changes when the absorbed hydrogen amount corresponds to a substantial zero occlude amount, and said calculating means judges a substantial zero occlude condition when detecting sudden change of the electrical resistance value.

5. An absorbed hydrogen amount detecting apparatus according to claim 2, wherein said calculating means memorizes a map showing a relation between the electrical resistance value and the absorbed hydrogen amount, and determines a present absorbed hydrogen amount based on the detected electrical resistance value and the map.

6. An absorbed hydrogen amount detecting apparatus according to claim 2, wherein said hydrogen absorbing tank is comprised of a capsule for detecting the absorbed hydrogen amount contained in a main tank in which a large amount of the hydrogen absorbing alloy powder is contained so that a hydrogen gas comes in said hydrogen absorbing tank from an external and goes out therefrom to the external.

7. An absorbed hydrogen amount detecting apparatus according to claim 5, wherein said hydrogen absorbing tank is comprised of a capsule for detecting the absorbed hydrogen amount contained in a main tank in which a large amount of the hydrogen absorbing alloy powder is contained so that a hydrogen gas comes in said hydrogen absorbing tank from an external and goes out therefrom to the external.

8. A hydrogen occlude detecting apparatus according to claim 6, wherein said hydrogen absorbing tank includes a first hydrogen absorbing tank containing the amount of the hydrogen absorbing alloy powder in which the electrical resistance value suddenly changes when the absorbed hydrogen amount corresponds to a saturate amount substantially, and a second hydrogen absorbing tank containing the amount of the hydrogen absorbing alloy powder in which the electrical resistance value suddenly changes when the absorbed hydrogen amount corresponds to zero substantially;

said calculating means determines the substantial hydrogen occlude saturate condition when detecting the sudden change of the electrical resistance value between the both electrodes in the first hydrogen absorbing tank, and determines the substantial hydrogen occlude zero condition when detecting the sudden change of the electrical resistance value between the both electrodes in the second hydrogen absorbing tank.

9. A hydrogen occlude detecting apparatus according to claim 8, wherein one of the first hydrogen absorbing tank and the second hydrogen absorbing tank comprises said main tank.

10. An absorbed hydrogen amount detecting apparatus according to claim 3, wherein said calculating means memorizes a map showing a relation between the electrical resistance value and the absorbed hydrogen amount, and determines a present absorbed hydrogen amount based on the detected electrical resistance value and the map.

11. An absorbed hydrogen amount detecting apparatus according to claim 4, wherein said calculating means memorizes a map showing a relation between the electrical resistance value and the absorbed hydrogen amount, and determines a present absorbed hydrogen amount based on the detected electrical resistance value and the map.

12. An absorbed hydrogen amount detecting apparatus according to claim 3, wherein said hydrogen absorbing tank is comprised of a capsule for detecting the absorbed hydrogen amount contained in a main tank in which a large amount of the hydrogen absorbing alloy powder is contained so that a hydrogen gas comes in said hydrogen absorbing tank from an external and goes out therefrom to the external.

13. An absorbed hydrogen amount detecting apparatus according to claim 4, wherein said hydrogen absorbing tank is comprised of a capsule for detecting the absorbed hydrogen amount contained in a main tank in which a large amount of the hydrogen absorbing alloy powder is contained so that a hydrogen gas comes in said hydrogen absorbing tank from an external and goes out therefrom to the external.

14. An absorbed hydrogen amount detecting apparatus according to claim 6, wherein said hydrogen absorbing tank is comprised of a capsule for detecting the absorbed hydrogen amount contained in a main tank in which a large amount of the hydrogen absorbing alloy powder is contained so that a hydrogen gas comes in said hydrogen absorbing tank from an external and goes out therefrom to the external.

15. A hydrogen occlude detecting apparatus according to claim 7, wherein said hydrogen absorbing tank includes a first hydrogen absorbing tank containing the amount of the hydrogen absorbing alloy powder in which the electrical resistance value suddenly changes when the absorbed hydrogen amount corresponds to a saturate amount substantially, and a second hydrogen absorbing tank containing the amount of the hydrogen absorbing alloy powder in which the electrical resistance value suddenly changes when the absorbed hydrogen amount corresponds to zero substantially;

said calculating means determines the substantial hydrogen occlude saturate condition when detecting the sudden change of the electrical resistance value between the both electrodes in the first hydrogen absorbing tank, and determines the substantial hydrogen occlude zero condition when detecting the sudden change of the electrical resistance value between the both electrodes in the second hydrogen absorbing tank.

\* \* \* \* \*